United States Patent [19]

Estreicher et al.

[11] Patent Number: 4,582,529

[45] Date of Patent: Apr. 15, 1986

[54] USE OF CERTAIN ACETYLENE-SUBSTITUTED AMINO-ACID COMPOUNDS FOR CONTROLLING THE GROWTH OF UNWANTED PLANTS

[76] Inventors: Herbert Estreicher, 3901 Hillsboro Ct., Modesto, Calif. 95352; Dennis H. Flint, 1316 Amy Ave., Modesto, Calif. 95355; Richard B. Silverman, 2921 W. Chase Ave., Chicago, Ill. 60645

[21] Appl. No.: 680,031

[22] Filed: Dec. 10, 1984

Related U.S. Application Data

[63] Continuation-in-part of Ser. No. 550,433, Nov. 11, 1983, abandoned.

[51] Int. Cl.$^4$ .................... A01N 37/02; A01N 37/06; A01N 37/18
[52] U.S. Cl. ........................ 71/113; 71/106; 71/118; 71/DIG. 2
[58] Field of Search .................... 71/113, 106, 118

[56] References Cited

U.S. PATENT DOCUMENTS 3,517,041  6/1970  Scharr et al. ............... 71/113 X
4,164,403  8/1979  Ehrenfreund ............... 71/113 X

*Primary Examiner*—Catherine L. Mills

[57] ABSTRACT

Growth of unwanted plants is controlled by certain acetylene-substituted aminocarboxylic acid compounds.

2 Claims, No Drawings

USE OF CERTAIN ACETYLENE-SUBSTITUTED AMINO-ACID COMPOUNDS FOR CONTROLLING THE GROWTH OF UNWANTED PLANTS

This application is a continuation-in-part of co-pending application Ser. No. 550,433, filed on Nov. 11, 1983, abandoned.

DESCRIPTION OF THE INVENTION

It has been found that the growth of plants is adversely affected by acetylene-substituted aminocarboxylic acids, and derivatives thereof of the formula:

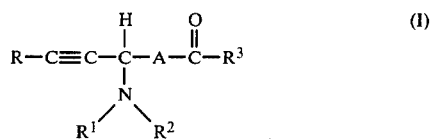

wherein R is hydrogen, methyl or ethyl, A is $-CH_2-$, $-CH_2-CH_2-$ or $-CH=CH-$; $R^3$ is $-OH$, $-OR^4$ or $-NH_2$ or $-NHR^4$, wherein $R^4$ is alkyl of one to six carbon atoms; $R^1$ is hydrogen, $R^2$ is hydrogen or $-C(O)OR^5$, wherein $R^5$ is alkyl of one to six carbon atoms optionally substituted by halogen, or is phenyl or benzyl optionally substituted by from one to three of one or more of halogen, nitro, hydroxyl and alkyl, alkoxy and alkylthio of from one to four carbon atoms, or $R^1$ and $R^2$ together are the two bonds of an alkylidene moiety

wherein $R^6$ is a phenyl moiety represented by $R^5$.

In these compounds, each alkyl moiety suitably is either straight-chain or branched-chain in configuration. The term "halogen" designates one of chlorine, bromine and fluorine.

Because of its phytotoxicity, a preferred individual species of the compounds of Formula I is that wherein R, $R^1$ and $R^2$ each is hydrogen, $R^3$ is hydroxyl and A is $-CH_2-CH_2-$.

Salts of these compounds also are contemplated, suitable salts being those of alkali metals, alkaline earth metals, amines, and ammonia, and, where $R^1$ and $R^2$ both are hydrogen, the hydrohalide salts. Suitable amine salts include those of mono-, di- and tri-alkyl- and alkanolamines wherein each alkyl moiety contains up to 20 carbon atoms.

Since the carbon atom of the amino acid to which the amino moiety is bonded is a chiral center, the compounds can exist in the form of optical isomers. The activities of the individual isomers with respect to plants may differ, and in the cases of the individual species of the compounds of Formula I whose preparation is described in the examples, hereinafter, the isomeric content of the products has not been ascertained. The invention contemplates all of the active isomers and mixtures containing them, both those which result from the method of synthesis, and those which have been created deliberately.

Compounds of Formula I wherein R is hydrogen are known compounds, being disclosed, together with a method for their preparation, in U.S. Pat. No. 4,041,041.

By this method, the acids or their esters can be prepared. Also, an acid can be prepared from the ester, or vice versa, by conventional methods. Amides ($R^3=-NH_2$, or $-NHR^4$) can be prepared from the corresponding acids by conventional methods. In the method of the patent, preparation of compounds of Formula I where R is hydrogen requires a precursor in which the hydrogen atom R is reactive. To avoid reaction at that site, the hydrogen atom R of the precursor is replaced by a trimethylsilyl moiety, which acts as a protecting group and later in the method is removed and replaced by a hydrogen atom. The corresponding compounds of Formula I wherein R is methyl or ethyl can be prepared directly from the respective precursors, the methyl and ethyl moieties themselves acting as if they are protecting groups.

Synthesis, isolation and characterization of individual species of Formula I, in particular instances, are described in the following examples. In these examples, the identity of each product, and of each intermediate involved, was confirmed by appropriate chemical and spectral analyses.

EXAMPLE 1

Ethyl 4-amino-5-hexynoate hydrochloride (1)

10 g of magnesium sulfate was added to a stirred solution of 13.8 g of propargylamine and 26.5 g of benzaldehyde in 75 ml of benzene and the resulting mixture was stirred at room temperature for 30 minutes. The mixture then was filtered and water was removed from the filtrate by azeotropic distillation. Then the remaining benzene was evaporated and the residue was distilled to give N-benzylidene-2-propyn-1-amine (1A) b.p.: 64°-66° C. (0.2 Torr.).

10 g of ethyl magnesium bromide was added over 30 minutes to a stirred solution of 10.2 g of 1A in 100 ml of tetrahydrofuran at 0° C. The resulting mixture was stirred at that temperature for 30 minutes, then a solution of 7.75 g of trimethylsilyl chloride in 30 ml of tetrahydrofuran was added over 30 minutes. The mixture then was stirred at 0° C. for 90 minutes, treated with brine, dried (MgSO4) and the solvent was evaporated. The residue was distilled at 85°-90° C., 0.3 Torr., to give N-benzylidene-3-(trimethylsilyl)-2-propyn-1-amine (1B), as a water-white oil.

13.4 ml of a 1.6M solution of n-butyllithium in hexane was added drop-by-drop over two minutes to a solution of 4.5 g of 1B in 200 ml of tetrahydrofuran at −70° C. After 20 minutes at −70° C., 1.8 g of freshly distilled methyl acrylate was added and the mixture was allowed to warm slowly to room temperature. The solvent was evaporated and a solution of 8 ml of concentrated hydrochloric acid in 60 ml of water was added to the residue. The resulting mixture was heated at reflux for 20 hours and cooled. The aqueous phase was separated and washed with methylene chloride, adjusted to a pH of 8 and extracted with methylene chloride. The aqueous phase was adjusted to a pH of 6 and the water was evaporated. The residue (a solid) was ion exchange-chromatographed over Dowex 50 resin using 0.1N hydrochloric acid as eluent, to give a waxy solid. Crystallization from hot ethanol gave 1, as a white solid, m.p.: 110°-120° C.

EXAMPLE 2

4-amino-5-hexynoic acid hydrochloride (2)

A solution of 0.4 g of 1 in 2 ml of concentrated hydrochloric acid was stirred at room temperature for one hour. The water was evaporated. Toluene was added to the residue and distilled to remove residual water by azeotropic distillation. The residue was dried under reduced pressure to give 2, as a hygroscopic solid.

EXAMPLE 3

Methyl 4-amino-5-hexynoate (3)

53.6 ml of a 1.6M solution of n-butyllithium in hexane was added drop-by-drop over 20 minutes to a solution of 18.0 g of 1B in 700 ml of dry tetrahydrofuran at −70° C. The resulting mixture was stirred for 20 minutes at −70° C., when 7.2 g of freshly distilled methyl acrylate was added over 14 minutes. The resulting mixture was stirred for 30 minutes at −70° C., when 16.5 ml of water was added drop-by-drop. The resulting mixture was allowed to warm slowly to room temperature; the solvent was evaporated; the residue was diluted with water and the resulting mixture was extracted with ether. The ether extract was washed with brine, dried ($Na_2SO_4$), filtered and the solvent was evaporated. The residue (a dark thick oil) was distilled in a Kugelrohr apparatus to give methyl 6-(trimethylsilyl)-4-(benzylideneamino)-5-hexynoate (3A), b.p.: 140°–142° C. (0.01 Torr.).

0.1 g of sodium was dissolved in 10 ml of methanol, under nitrogen. 1.5 g of 3A was stirred in 12 ml of dry methanol at 0° C. under nitrogen and 0.23 ml of the sodium methoxide solution was added drop-by-drop at 0° C. The resulting mixture was stirred at 0° C. for 3.5 hours, then stored in a freezer over a week-end. Then 30 mg of ammonium chloride was added, the mixture was stirred for 15 minutes at 0° C., stripped to a mush, slurried with ether and filtered. The ether was evaporated from the filtrate, the residue was dissolved in 25 ml of tetrahydrofuran and the solution was added drop-by-drop over one minute to a vigorously stirred ice-cold 0.2N hydrochloric acid solution. The resulting mixture was stirred at 0° C. for 3.5 hours, the solvent was evaporated and the residue was extracted with ether. The water was evaporated from the aqueous phase, toluene was added to the residue and residual water removed by azeotropic distillation. The residue was dissolved in methanol, toluene was added and the mixture was distilled azeotropically. The residue was dissolved in methylene chloride, the solution was dried ($Na_2SO_4$), filtered and the solvent was evaporated. The residue was subjected to low pressure distillation, to give 3, as a gum.

EXAMPLE 4 methyl 4-(benzylideneamino)-5-hexynoate (4)

0.0764 g of sodium was dissolved in 5 ml of methanol. The solution was added at room temperature to a solution of 1.0 g of 3A in 2 ml of dry methanol. The mixture was stirred at room temperature for 4 hours, then 0.1765 g of ammonium chloride was added and the mixture was stirred for 15 minutes. Then the methanol was evaporated, the residue was triturated with ether and the solid phase was filtered off. The solvent was evaporated from the filtrate and the residue was distilled to give 4, b.p.: 170° C. (0.07 Torr).

EXAMPLE 5

3-amino-4-pentynoic acid (5)

A solution of 17.6 g of 1B in 300 ml of dry tetrahydrofuran was added drop-by-drop to a solution of lithium diisopropylamide (prepared by adding 38 ml of a 2.2M solution of n-butyllithium in hexane to a solution of 11 ml of diisopropylamine and 12 ml of tetramethylethylenediamine in 450 ml of tetrahydrofuran) at −78° C. under argon. The resulting solution was held at −78° C. for 40 minutes, then a solution of 13.5 ml of tert-butyl bromoacetate in 50 ml of dry tetrahydrofuran was added. The resulting mixture was stirred at −78° C. for 30 minutes, at 0° C. for 10 minutes, then was poured into 300 ml of ice water containing 4.5 g of ammonium chloride. The resulting mixture was extracted with ether, the extract was washed with water, treated with charcoal and the solvent was evaporated. The residue was stirred in a solution of 7.5 g of sodium methoxide in 700 ml of methanol for 24 hours at room temperature. Then the solvent was evaporated and the residue was mixed with 200 ml of water containing 7.5 g of ammonium chloride. The mixture was extracted with ether, the extract was washed with water, dried ($MgSO_4$) and the solvent was evaporated to give tert-butyl 3-(benzylideneamino)-4-pentynoate (5A), as a brown oil.

A mixture of a solution of 17 g of 5A in 200 ml of tetrahydrofuran and 200 ml of 4N hydrochloric acid was stirred for 20 hours at room temperature. Then the solvents were evaporated below 40° C. The residue was taken up in water, the solution was washed successively with chloroform and ether, then applied to a column of Dowex 50 (H+)(120 ml). The column was washed with water until the eluate was neutral, then the amino acid was eluted with 1N ammonium hydroxide. Evaporation of the solvent from the eluate under 40° C., and recrystallization of the residue from water/acetone gave 5, as an off-white solid, m.p.: 199°–200° C.

Compounds of Formula I have been found to affect adversely the growth of plants, and therefore to be useful for controlling the growth of unwanted plants.

Accordingly, the invention includes a method of combatting unwanted plants which comprises applying to the locus an effective amount of a compound of Formula I. For application, the compound generally is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water, alcohols such as, for example, isopropanol, glycols; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain, in addition to the solid carrier, 3–10% by weight of a dispersing agent, 15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to that solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

In the following examples, the species of plants that were tested were:
Barnyardgrass (watergrass)—*Enchinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf *Abutilon theophrasti*
Garden cress—*Lepidium sativum*
Johnsongrass—*Sorghum halepense*

TEST PROCEDURES

The preemergence (soil) herbicidal activity of the compounds was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly-due to biological variability |
| 0 | No visible effect |

The postemergence (foliar) herbicidal activity of compounds of the invention was evaluated by spraying 10-day-old large downy brome plants in some cases, 6-day-old Johnsongrass plants in other cases, 9-day-old velvetleaf plants, 9-day-old yellow foxtail plants and 9-day-old sicklepod plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, and the effect of the test compound was then evaluated visually, the results being rated on the 0 to 9 scale described above.

Results of the preemergence and postemergence herbicidal activity tests are set forth in Table I.

TABLE I

| | HERBICIDAL ACTIVITY | | | | | | | | | | | |
|---|---|---|---|---|---|---|---|---|---|---|---|---|
| | Preemergence | | | | | | Postemergence | | | | | |
| Compound | Barnyard-grass | Garden cress | Downy brome | Velvet-leaf | Yellow foxtail | Sickle-pod | Crab-grass | Pig-weed | Johnson-grass | Velvet-leaf | Yellow foxtail | Sickle-pod |
| 1 | 9 | 9 | 7 | 7 | 7 | 8 | 7 | 7 | 4 | 3 | 2 | 3 |
| 2 | 9 | 9 | 9 | 9 | 9 | 9 | 7 | 7 | 6 | 5 | 5 | 5 |
| 3 | 9 | 9 | 2 | 7 | 3 | 8 | 7 | 7 | 3 | 2 | 2 | 4 |
| 4 | 9 | 8 | 2 | 3 | 2 | 8 | 7 | 7 | 0 | 0 | 0 | 0 |
| 5 | 7 | 7 | 3 | 6 | 2 | 5 | 8 | 4 | 3 | 3 | 2 | 2 |

We claim:

1. A method for controlling unwanted growth of plants at a locus which comprises applying to the locus an effective amount of a compound of the formula:

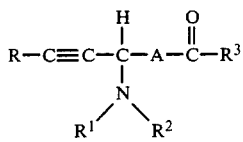

wherein R is hydrogen, methyl or ethyl, A is $-CH_2-$, $-CH_2-CH_2-$ or $-CH=CH-$; $R^3$ is $-OH$, $-OR^4$, or $-NH_2$ or $-NHR^4$, wherein $R^4$ is alkyl of one to six carbon atoms; $R^1$ and $R^2$ each is hydrogen, or $R^1$ and $R^2$ together are the two bonds of an alkylidene moiety

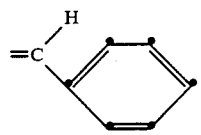

2. A method according to claim 1 in which the compound applied is the species of the formula wherein R, $R^1$ and $R^2$ each is hydrogen, $R^3$ is hydroxyl and A is $-CH_2-CH_2-$.

* * * * *